(12) United States Patent
Altman

(10) Patent No.: US 10,039,550 B2
(45) Date of Patent: Aug. 7, 2018

(54) MAGNETIC ANASTOMOSIS ASSEMBLY

(71) Applicant: Nir Altman, Kfar Etzion (IL)

(72) Inventor: Nir Altman, Kfar Etzion (IL)

(73) Assignee: Easy Notes Ltd., Kfar Truman (IL)

( * ) Notice: Subject to any disclaimer, the term of this patent is extended or adjusted under 35 U.S.C. 154(b) by 87 days.

(21) Appl. No.: 14/144,672

(22) Filed: Dec. 31, 2013

(65) Prior Publication Data

US 2015/0182224 A1 Jul. 2, 2015

(51) Int. Cl.
*A61B 17/08* (2006.01)
*A61B 17/11* (2006.01)
*A61B 17/00* (2006.01)

(52) U.S. Cl.
CPC ... *A61B 17/1114* (2013.01); *A61B 2017/0034* (2013.01); *A61B 2017/00278* (2013.01); *A61B 2017/00292* (2013.01); *A61B 2017/00477* (2013.01); *A61B 2017/00876* (2013.01); *A61B 2017/1117* (2013.01); *A61B 2017/1139* (2013.01)

(58) Field of Classification Search
CPC .... A61B 17/11; A61B 2017/1103–2017/1125; A61B 2017/1132–2017/1135; A61B 2017/1139; A61B 2017/1117; A61B 2017/00477; A61B 2017/00292; A61B 2017/00278; A61B 2017/0034; A61B 2017/00876

USPC .................................. 606/153, 129; 600/36
See application file for complete search history.

(56) References Cited

U.S. PATENT DOCUMENTS

| | | | |
|---|---|---|---|
| 7,706,861 B2 * | 4/2010 | Windheuser et al. | 600/434 |
| 2005/0182429 A1 * | 8/2005 | Yamanouchi | 606/153 |
| 2009/0125042 A1 * | 5/2009 | Mouw | 606/153 |
| 2009/0227828 A1 * | 9/2009 | Swain et al. | 600/12 |
| 2010/0292729 A1 * | 11/2010 | Aguirre et al. | 606/213 |
| 2013/0325042 A1 | 12/2013 | Fabian | |

FOREIGN PATENT DOCUMENTS

WO 2011/008988 1/2011

OTHER PUBLICATIONS

PCT Written Opinion PCT/US2014/072908, dated Mar. 23, 2015.

* cited by examiner

*Primary Examiner* — Diane Yabut
*Assistant Examiner* — Erich Herbermann
(74) *Attorney, Agent, or Firm* — Dekel Patent Ltd.; David Klein

(57) ABSTRACT

A magnetic anastomosis assembly includes a magnet with a passageway and a guidewire passing through the passageway. The passageway can be external or internal to the magnet body.

12 Claims, 3 Drawing Sheets

MAGNETIC ANASTOMOSIS ASSEMBLY

FIELD OF THE INVENTION

The present invention generally relates to devices and methods for creating an anastomosis in the gastrointestinal (GI) tract, and particularly to a magnetic anastomosis assembly that includes one or more magnets and a device for grasping the magnets for positioning relative to the pyloric valve (pylorus).

BACKGROUND OF THE INVENTION

Magnetic anastomosis devices are used to create a channel between two viscera for the purpose of redirecting bodily fluids. For example, intestinal contents or bile may be redirected in patients who have developed an obstruction of the bowel or bile duct due to such conditions as tumor, ulcer, inflammatory strictures or trauma. Some magnetic anastomosis devices include first and second magnet assemblies comprising magnetic cores that are surrounded by thin metal rims. Due to the magnetic attraction between the two magnetic cores, the walls of two adjacent viscera (e.g., the gall bladder, common bile duct, stomach, duodenum, or jejunum) may be sandwiched and compressed between the magnet assemblies, resulting in ischemic necrosis of the walls to produce an anastomosis between the two viscera. For example, one magnet may be placed in the stomach proximal to the pylorus and the other magnet placed distal to the pylorus in a portion of the small intestine (such as the duodenum, jejunum or ileum).

However, grasping the magnets for their proper positioning is not trivial. In particular, it is difficult to grasp and properly place the magnet that is distal to the pylorus so that it aligns properly with the magnet proximal to the pylorus.

SUMMARY OF THE INVENTION

The present invention seeks to provide a magnetic anastomosis assembly that includes one or more magnets and a device for grasping the magnets for positioning relative to the pylorus, as is described more in detail hereinbelow.

There is thus provided in accordance with an embodiment of the present invention a magnetic anastomosis assembly including a magnet with a passageway and a guidewire passing through the passageway. The passageway can be external or internal to the magnet body.

In accordance with an embodiment of the present invention the passageway includes an outwardly extending flange, the flange being formed with a lumen that has open ends through which the guidewire passes. The lumen may be closed transverse to the open ends, or alternatively, may have an open side portion transverse to the open ends. The magnet may have an elongate side upon which the flange is positioned.

In accordance with an embodiment of the present invention the magnet is at least partially disposed in a cover, and the flange extends outwards from the cover. The magnet or the cover may include a protruding rim.

In accordance with an embodiment of the present invention the assembly further includes a guidewire device that includes a cannula with a guidewire lumen. The cannula has a first portion spaced from a second portion by a gap, and the gap is dimensioned to at least partially receive therein the passageway of the magnet.

The assembly may further include a guidewire that passes through the guidewire lumens of the first and second portions of the cannula and passes through the passageway placed in the gap.

There is provided in accordance with an embodiment of the present invention a method including using the assembly to grasp the magnet by passing the guidewire through the guidewire lumens of the first and second portions of the cannula and through the passageway placed in the gap. The method further includes delivering the magnet to a place in a gastrointestinal tract and delivering another magnet to another place in the gastrointestinal tract, and aligning the magnets and releasing them so that magnetic forces attract the magnets together, compressing together walls of the gastrointestinal tract for eventually forming an anastomosis.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
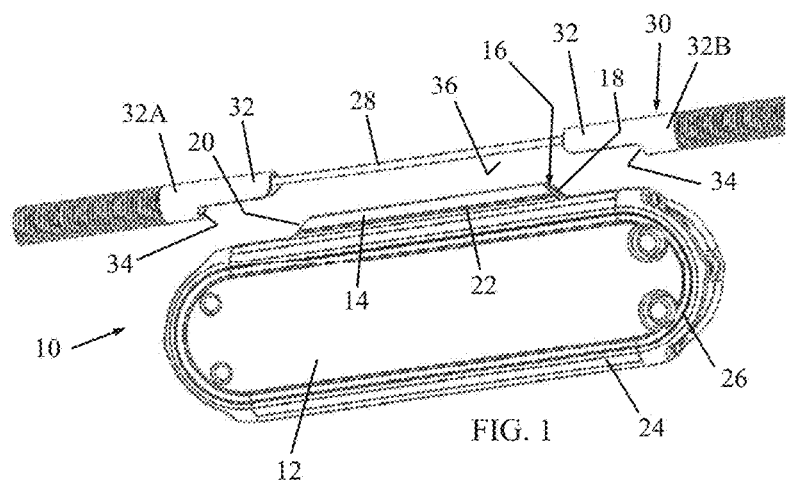
FIG. 1 is a simplified pictorial illustration of a magnetic anastomosis assembly, constructed and operative in accordance with an embodiment of the present invention, showing a magnet with an external passageway (e.g., an external flange) before grasping with a guidewire device.

Reference is now made to FIG. 1, which illustrates a magnetic anastomosis assembly 10, constructed and operative in accordance with a non-limiting embodiment of the present invention.

The assembly 10 includes a magnet 12 with an external passageway 14, such as an outwardly extending flange (referred to alternatively as flange 14). The term "external passageway" means that the passageway is external to the magnet body. Flange 14 is formed with a lumen 16 that has open ends 18 and 20 for passing therethrough a guidewire (not shown in FIG. 1, but seen later in FIG. 3). Lumen 16 may be a closed lumen, i.e., it is closed transverse to the open ends. Alternatively, lumen 16 may have an open side portion (indicated by numeral 22) transverse to the open ends. In such an alternative, the side opening 22 would be large enough for pushing a guidewire therethrough, but small enough so that the guidewire would not tend to move out of the lumen 16 through the side opening 22.

Magnet 12 is shown having a general oval disc shape, which means magnet 12 has an elongate side upon which flange 14 is positioned (flange 14 also being elongate). However, magnet 12 may have other shapes, such as but not limited to, cylindrical, polygonal, cube and others. "Elongate" in the description and claims means the length is greater than other dimensions (width or thickness), more preferably at least 25% greater than other dimensions, more preferably at least 100% greater than other dimensions, and most preferably at least 50% greater than other dimensions.

Magnet 12 may be at least partially disposed in a protective coating or cover 24 (such as, but not limited to, polytetrafluoroethylene) for protection of the magnetic core from corrosive digestive acids or other bodily fluids. The flange 14 extends outwards from the cover 24. The magnet 12 and/or the cover 24 may include a protruding rim 26, which may be useful in pinching tissue to form an anastomosis.

In accordance with an embodiment of the present invention, the assembly 10 further includes a guidewire device 30 that includes a cannula 32 (or tube, catheter and the like) with a guidewire lumen 34. In the illustrated embodiment, cannula 32 has a first adaptor portion 32A spaced from a second adaptor portion 32B by a gap 36. Gap 36 is dimensioned to at least partially receive therein flange 14. The first portion 32A of cannula 32 may be connected to the second portion 32B with a link member 28.

Figure 2:
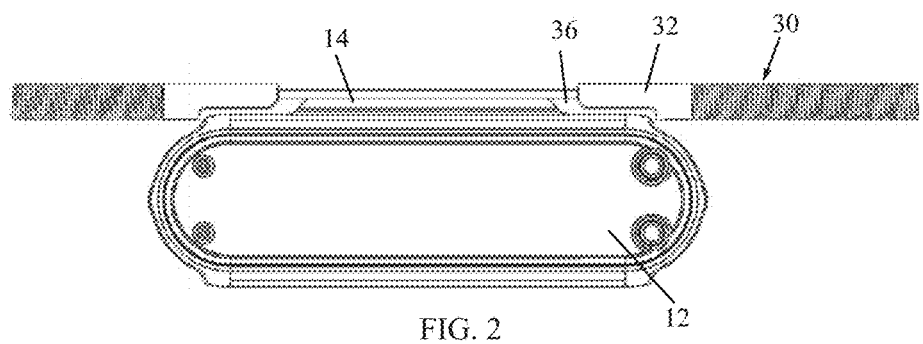
FIG. 2 is a simplified pictorial illustration of the magnet and flange placed in a gap of the guidewire device.
Figure 3:
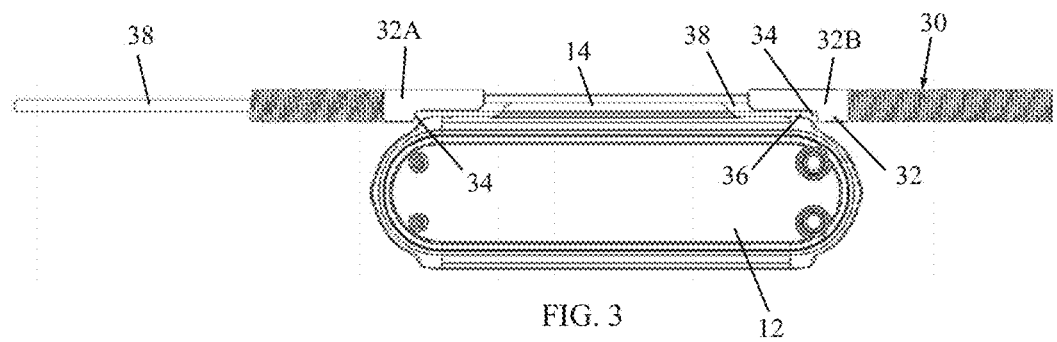
FIG. 3 is a simplified illustration of the guidewire device grasping the magnet.

In order to grasp the magnet 12, the user positions the guidewire device 30 next to magnet 12, so that flange 14 is received in gap 36, as seen in FIG. 2. As seen in FIG. 3, a guidewire 38 passes through the guidewire lumens 34 of the first and second portions of the cannula 32 and passes through the flange 14 placed in the gap 36. In this position, the magnet 12 is held by the guidewire 38 and cannot fall off the guidewire 38. The cannula 32 can be introduced through natural orifices for transluminal endoscopy. For example, after placing and holding the magnet 12 on the guidewire device 30, the guidewire device 30 can be introduced through the esophagus to the stomach and passed through the pylorus to a portion of the small intestine (such as the duodenum, jejunum or ileum). The guidewire 38 can be retracted proximally for releasing the magnet 12 at a desired location. The guidewire device 30 is much better suited for passing through the small constriction of the pylorus; it is normally difficult to grasp a magnet on the distal side of the pylorus with prior art tools.

Another magnet can be delivered to a corresponding place in the stomach by grasping with the guidewire device 30 (or other grasping tool) so that after releasing, the two magnets are aligned with each other, one in the stomach and the other in the small intestine. The magnetic forces attract the magnets together, compressing together walls of the gastrointestinal tract for eventually forming an anastomosis. The walls may be pinched by the protruding rims of the magnets.

In one embodiment, the "other grasping tool" may be a needle-nose pliers or other suitable grasping tool which is normally closed, that is, the user must exert force to open the jaws of the tool and exert no external force for the jaws to close and squeeze against the magnet that is being held. Such a tool is advantageous because the user can easily grasp the other magnet without having to exert force all the while the magnet is held. Such a grasping tool may be used for the magnet which is placed in the GI tract outside of the stomach as well. An external magnet placed on or near the patient's body may be used to move the two internal magnets together to cause the internal magnets to align and compress the tissue together to eventually form the anastomosis.

Figure 4A:
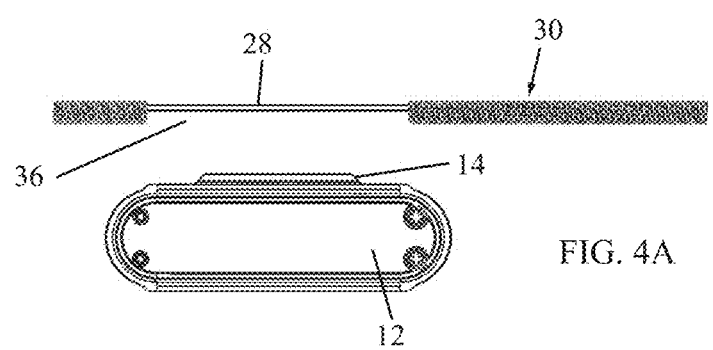
FIGS. 4A and 4B are simplified pictorial illustrations of a magnetic anastomosis assembly, constructed and operative in accordance with another embodiment of the present invention, respectively before and after the magnet with the flange is grasped with a guidewire device.
Figure 4B:
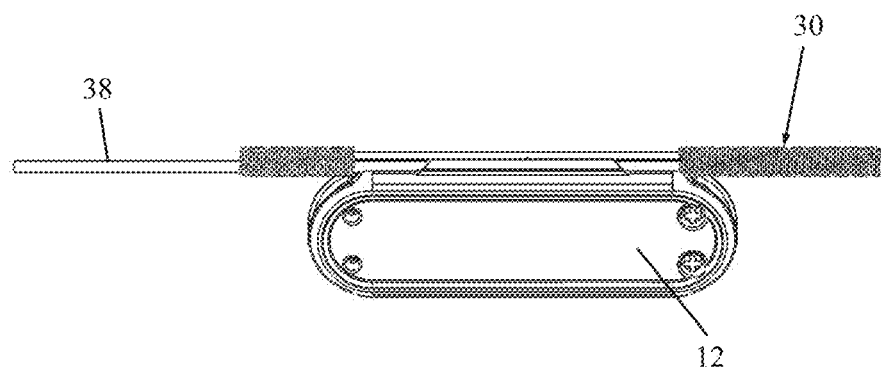

Reference is now made to FIGS. 4A and 4B, which illustrate another version of the magnetic anastomosis assembly. This embodiment differs from the previous embodiment by not having adaptor portions in the guidewire device 30.

Figure 5:
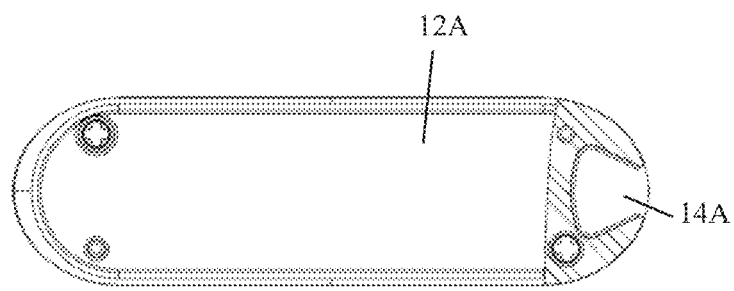
FIG. 5 is a simplified sectional illustration of a magnetic anastomosis assembly, constructed and operative in accordance with yet another embodiment of the present invention, showing a magnet with an external passageway on a short side of the magnet.

In the previous embodiment, flange 14 extends along the long dimension (length) of magnet 12. Reference is now made to FIG. 5, which illustrates a magnet 12A with an external passageway 14A on a short side of the magnet 12A. The external passageway can be positioned in other ways, too, such as diagonally across the magnet.

Figure 6A:
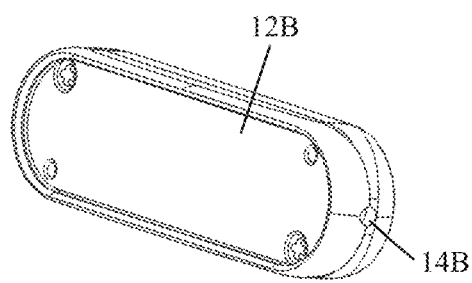
FIGS. 6A and 6B are simplified pictorial illustrations of a magnetic anastomosis assembly wherein the magnet has an internal lumen (e.g., a central longitudinal lumen), constructed and operative in accordance with another embodiment of the present invention, respectively before and after the magnet is grasped with a guidewire device.
Figure 6B:
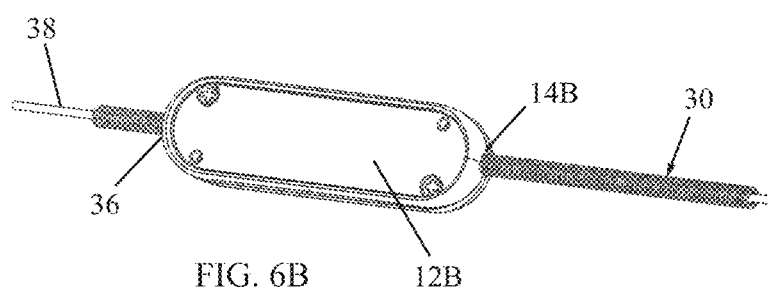

Reference is now made to FIGS. 6A and 6B, which illustrate a magnetic anastomosis assembly, constructed and operative in accordance with another embodiment of the present invention. In this embodiment, a magnet 12B has an internal passageway or lumen 14B (e.g., a central longitudinal passageway) through which the guidewire 38 of guidewire device 30 can pass. The term "internal passageway" means that the passageway is internal to the magnet body. The internal passageway 14B may be surrounded by magnetic material (such as a hole drilled through the magnet 12B). Alternatively, the internal passageway 14B may include a bushing or sleeve inserted in a hole drilled through the magnet 12B. Here again the gap 36 is dimensioned to at least partially receive therein passageway 14B of magnet 12B.

What is claimed is:

1. An assembly comprising:
   a magnet with an external passageway and a guidewire, which supports said magnet, passing through said passageway, said external passageway comprising an outwardly extending flange which is formed with a lumen that has open ends through which said guidewire passes;
   a guidewire device that comprises a cannula with a guidewire lumen, said cannula comprising a first adaptor portion spaced from a second adaptor portion by a gap, said gap being dimensioned to at least partially receive therein said flange, and wherein said first and second adaptor portions are connected to each other with a link member; and
   said guidewire passes through said guidewire lumen of said first and second adaptor portions of said cannula and passes through said flange placed in said gap, wherein said magnet is held by said guidewire and cannot fall off said guidewire, and wherein surfaces of said first and second adaptor portions prevent said magnet from moving axially along said guidewire, said surfaces comprising left and right shoulders on said cannula at opposite ends of said gap;
   and a protrusion, separate from said guidewire, that extends from said magnet to said flange, said protrusion extending axially beyond left and right sides of said flange, and said protrusion having left and right end faces configured to abut against said left and right shoulders.

2. The assembly according to claim 1, wherein said magnet has long and short sides and said passageway is positioned on the long side.

3. The assembly according to claim 1, wherein said magnet is at least partially disposed in a cover, and said passageway extends outwards from said cover.

4. The assembly according to claim 3, wherein said magnet or said cover comprises a protruding rim.

5. The assembly according to claim 1, wherein said lumen has a side opening transverse to said open ends, and said side opening is large enough for pushing said guidewire therethrough, but small enough so that said guidewire does not tend to move out of said lumen through said side opening.

6. The assembly according to claim 1, wherein said guidewire is parallel to said link member, said flange and said protrusion along their full lengths.

7. The assembly according to claim 1, wherein said protrusion is parallel to said guidewire.

8. The assembly according to claim 1, wherein said protrusion protrudes out of a face of said magnet which is parallel to said guidewire.

9. The assembly according to claim 1, wherein said protrusion is located between said flange and said magnet.

10. The assembly according to claim 1, wherein said protrusion is located between said flange and said magnet, wherein said flange is axially shorter than said protrusion and said protrusion is axially shorter than said magnet.

11. A method comprising using the assembly of claim 1 to grasp the magnet by passing the guidewire through said guidewire lumen of the first and second adaptor portions of said cannula and through said passageway placed in said gap.

12. The method according to claim 11, further comprising delivering said magnet to a place in a gastrointestinal tract and delivering another magnet to another place in the gastrointestinal tract, and aligning said magnets and releasing them so that magnetic forces attract said magnets together, compressing together walls of the gastrointestinal tract for eventually forming an anastomosis.

\* \* \* \* \*